United States Patent
Hauge (10) Patent No.: US 8,443,797 B2
(45) Date of Patent: May 21, 2013

(54) APPARATUS FOR MAINTAINING A SURGICAL AIRWAY AND METHOD OF THE SAME

(76) Inventor: Russ Hauge, Woodbury, MN (US)

( * ) Notice: Subject to any disclaimer, the term of this patent is extended or adjusted under 35 U.S.C. 154(b) by 848 days.

(21) Appl. No.: 12/519,972

(22) PCT Filed: Dec. 18, 2007

(86) PCT No.: PCT/US2007/087920
§ 371 (c)(1),
(2), (4) Date: Nov. 24, 2009

(87) PCT Pub. No.: WO2008/077033
PCT Pub. Date: Jun. 26, 2008

(65) Prior Publication Data
US 2010/0101567 A1    Apr. 29, 2010

Related U.S. Application Data

(60) Provisional application No. 60/875,429, filed on Dec. 18, 2006.

(51) Int. Cl.
*A61M 16/00*    (2006.01)

(52) U.S. Cl.
USPC ............. 128/200.26; 128/207.14; 128/207.15

(58) Field of Classification Search
USPC ............. 128/200.26, 201.26, 206.29, 207.11, 128/207.14, 207.15, 207.17, 207.29
See application file for complete search history.

(56) References Cited

U.S. PATENT DOCUMENTS

| 2,127,215 | A |   | 8/1938  | Gwathmey |
|-----------|---|---|---------|----------|
| 2,820,457 | A |   | 1/1958  | Phillips |
| 3,908,665 | A | * | 9/1975  | Moses ...................... 128/207.14 |
| 5,474,063 | A |   | 12/1995 | Riendeau |
| 5,653,229 | A |   | 8/1997  | Greenberg |
| 5,937,858 | A | * | 8/1999  | Connell .................... 128/207.14 |
| 5,950,624 | A |   | 9/1999  | Hart |
| 6,098,617 | A | * | 8/2000  | Connell .................... 128/200.26 |
| 6,256,524 | B1|   | 7/2001  | Walker et al. |

(Continued)

FOREIGN PATENT DOCUMENTS

| DE | 19734821 A1      | 2/1999  |
| WO | WO 99/07428 A1   | 2/1999  |
| WO | WO 02/055143 A2  | 7/2002  |
| WO | WO 2006/132940 A1| 12/2006 |

OTHER PUBLICATIONS

International Search Report of PCT/US2007/087920, dated Jun. 4, 2008.
Written Opinion of the International Searching Authority of PCT/US2007/087920, dated Jun. 4, 2008.

*Primary Examiner* — Steven Douglas
(74) *Attorney, Agent, or Firm* — Hamre, Schumann, Mueller & Larson, P.C.

(57) ABSTRACT

An apparatus for maintaining a surgical airway and method for the same includes an elongated body insertable orally into a patient. The elongated body defines leading and trailing ends. An opening is defined through the leading and trailing ends, such that surgical equipment may be insertable through the opening of the elongated body. A securing member is connected to the trailing end. The securing member holds the elongated body in a position such that an airway remains open to treat the patient, while supporting oxygen flow to the patient.

4 Claims, 9 Drawing Sheets

U.S. PATENT DOCUMENTS

| | | |
|---|---|---|
| 2003/0000534 A1 | 1/2003 | Alfery |
| 2003/0034036 A1 | 2/2003 | Waldeck |
| 2004/0129272 A1 | 7/2004 | Ganesh et al. |
| 2004/0221851 A1 | 11/2004 | Madsen |

* cited by examiner

APPARATUS FOR MAINTAINING A SURGICAL AIRWAY AND METHOD OF THE SAME

CROSS-REFERENCE TO RELATED APPLICATIONS

This application is being filed as a PCT International Application in the name of Russ Hauge and claims the benefit of U.S. Provisional Patent Application Ser. No. 60/875,429, filed Dec. 18, 2006, entitled "APPARATUS FUR MAINTAINING A SURGICAL AIRWAY AND METHOD OF THE SAME."

FIELD

The invention relates to an apparatus for maintaining a surgical airway and method of the same. More particularly, an apparatus is disclosed that is to be inserted into and held within a patient's mouth.

BACKGROUND

Devices for maintaining a surgical airway are well known and widely used, such as for enabling a patient to continue breathing during surgical and outpatient procedures. Typically, such devices may be employed in gastro and/or bronchial surgical procedures, and may be employed in outpatient applications, for instance, where patients experience sleep apnea.

In previous applications, a nasal cannula and bite block combination have been used. However, difficulties arise where a patient does not have a nasal airway or cannot breathe through his/her nose. Employing a nasal cannula and bite block limits the flow of oxygen to a patient. Such devices only deliver 28%-40% oxygen concentration to the patient. Furthermore, the bite block may not be optimally secured, and thus may not always stay in place. Such devices also require extensive modification to be capable of monitoring carbon dioxide.

While these previous applications have provided some advancement for maintaining a surgical airway, improvements may yet be made to such devices. There is a need for improving an apparatus for maintaining a surgical airway that provides optimal oxygen flow, and that has the capability to monitor and detect end tidal carbon dioxide ($ETCO_2$). A device is desirable that can be better secured so as to stay in place, while sufficiently maintaining access to the airway. Improvements may still be made to an apparatus for maintaining a surgical airway that requires less equipment and that can be conveniently used.

SUMMARY

It is the purpose in the descriptions hereafter to overcome these difficulties, thereby providing an improved apparatus for maintaining a surgical airway and method for the same.

In one embodiment, an apparatus for maintaining a surgical airway includes an elongated body insertable orally into a patient. The elongated body defines leading and trailing ends. An opening is defined through the leading and trailing ends, such that surgical equipment may be insertable into the elongated body and through the opening. A securing member is connected to the trailing end. The securing member holds the elongated body in a position such that an airway remains open to treat the patient while supporting oxygen flow to the patient.

In one embodiment, an apparatus for maintaining a surgical airway includes an extended portion connected to the trailing end of the elongated body. The extended portion is configured to be at least partially disposed at a position corresponding externally to a mouth of the patient. The extended portion defines an access to the opening.

In one embodiment, an apparatus for maintaining a surgical airway includes at least one securing member support. The securing member support engages the securing member to hold the elongated body in a position such that an airway of the patient remains open.

In another embodiment, an apparatus for maintaining a surgical airway defines at least one aperture therethrough. The aperture(s) enable access to at least one flow channel. Preferably, the flow channels are formed within the elongated body and are capable of delivering fluids to the patient and/or monitoring fluid release from the patient, for example delivering supplemented oxygen or monitoring end tidal carbon dioxide.

In yet another embodiment, the elongated body defines an arching portion proximate the leading end. The arching portion enables the elongated body to maintain the tongue of the patient in a posterior position, so as to prevent a gag reflex when the elongated body is inserted.

The apparatus may be constructed and arranged for one-time use.

The apparatus for maintaining a surgical airway provides an improved surgical airway. The apparatus provides a more secure surgical airway that may be disposed after one-time use. The elongated body provides a structure that includes bite block protection and keeps the tongue from obstructing the airway (oral pharynx). The apparatus is capable for monitoring end tidal carbon dioxide release of a patient, so that oxygen may be delivered sooner to the patient. The apparatus also provides supplemental oxygen flow to the patient at a higher concentration and at improved rates without impeding access to the airway.

The apparatus may be employed in various applications requiring maintenance of a surgical airway. Such applications include esophago-gastro dilatations (EGDs), gastroscopies, bronchoscopies, and deep monitored anesthesia care (MAC) cases. The apparatus further aids in other outpatient procedures, such as those patients suffering from sleep apnea. The apparatus for maintaining a surgical airway requires less equipment for use, for example, no mask is required to cover a patient's face. The apparatus provides an elegant design with improved performance and user convenience.

These and other various advantages and features of novelty, which characterize the apparatus for maintaining a surgical airway, are pointed out in the following detailed description. For better understanding of the apparatus, its advantages, and the objects obtained by its use, reference should also be made to the drawings which form a further part hereof, and to the accompanying descriptive matter, in which there are illustrated and described specific examples of the apparatus.

BRIEF DESCRIPTION OF THE DRAWINGS

Like reference numbers generally indicate corresponding elements in the Figures. The embodiments illustrated are exemplary only and are in accordance with the inventive principles described herein.

DETAILED DESCRIPTION OF THE PREFERRED EMBODIMENT

One exemplary embodiment of an apparatus for maintaining a surgical airway 10 is provided in FIGS. 1-5. The apparatus 10 is similar to that disclosed in pending U.S. application Ser. No. 11/445,797 filed on Jun. 2, 2006, which is incorporated herewith in its entirety.

The apparatus for maintaining a surgical airway 10 (hereafter the apparatus) includes an elongated body 12 defining first and second ends. The elongated body 12 is insertable orally into a mouth of a patient. One of the first or second ends of the elongated body 12 defines a leading end 14. The other of the first or second ends defines a trailing end 16. The leading end 14 is orally insertable into the patient with the trailing end 16 being orally insertable behind the leading end 14. Disposed proximately to the leading end 14, the elongated body 12 includes a lead portion 18. Disposed proximately to the trailing end 16, the elongated body includes a trail portion 19. The lead portion 18 and trail portion 19 will be further discussed below.

An opening 17 is defined through the leading and trailing ends 14, 16. Preferably, surgical equipment may be insertable into the elongated body 12 through the opening 17. In some preferred applications, such as in gastro and/or bronchoscope procedures or as in suctioning procedures, the opening 17 enables treatment of the patient through the opening 17 with the required medical instruments. The opening 17 provides an airway to be maintained open when the elongated body 12 is inserted orally into the patient. The opening 17 thus enables insertion of treatment instruments, and supports airflow and oxygen flow to the patient for him/her to breathe.

A securing member 30 is connected to the trailing end 16. The securing member 30 holds the elongated body 12 in position during use, and prevents dislodgment of the same. As one exemplary embodiment, the securing member 30 may be a resilient strap with elastic physical characteristics. The securing member 30 may include a plurality of securing holes 32 therethrough and along a side surface of the strap. The securing holes 32 removably attach with a support on the elongated body 12 or suitable adapter (described below) that may be used in connection with the elongated body 12. As one preferred example, opposing ends of the securing member 30 are removably attached proximate the trailing end 16 of the elongated body 12 by the securing holes 32.

When the elongated body 12 is inserted orally into a patient, the securing member 30, attached to the elongated body 30 may be dressed around a patient's neck or lower head to secure the apparatus 10. The plurality of securing holes 32 enables fine adjustment of the securing member 30, so as to provide an optimal and comfortable fit for the patient. The securing member 30 thus stabilizes the elongated body 12, such that the opening 17 can maintain an open airway of the patient for treatment, while supporting oxygen flow to the patient.

The elongated body 12 may be constructed of any number of materials, including but not limited to molded softer plastics. It will be appreciated that such materials are exemplary only, as other materials may be equally or more suitable. As one preferred example, the material(s) used to construct the elongated body are medically approved. It will be further appreciated that the elongated body 12 may be limited only to the extent in providing a suitably rigid elongated body structure that does not collapse or cannot be bitten down on while maintaining an open airway of the patient.

The securing member 30 may be constructed of any number of materials, including but not limited to a soft elastic rubber. It will be appreciated that such materials are exemplary only, as other materials may be equally suitable. As one preferred example, the material(s) used to construct the securing member are medically approved. The material employed for constructing the securing member 30 may only be limited by such physical characteristics necessary for securing the elongated body 12 as described, and for providing a comfortable fit around a patient's neck or lower head.

In another embodiment for the apparatus for maintaining a surgical airway 10, an adapter 20 is connected to the trailing end 16 of the elongated body 12. In one preferred example, the adapter 20 may be inserted into the opening 17 of the elongated body 12 at the trailing end 16, and is configured to be at least partially disposed external to a mouth of the patient, when the apparatus is inserted into a patient's mouth. The adapter 20 includes an access 27 to the opening 17, such that surgical equipment may be inserted into the access 27 to reach the opening 17 of the elongated body 12. Preferably, the access 27 may be defined by an extended portion 28. The extended portion 28 provides a structure that extends outward from the mouth of a patient, so that the access 27 may enable insertion of surgical equipment into the opening 17.

As one example only, the extended portion 28 is illustrated as a hollow cylindrical structure defining the access 27. It will be appreciated, however, that such a configuration is exemplary only, as other configurations and shapes may be equally or more suitable. As other non-limiting examples, the extended portion may be an oval-like or other arcuate shape.

In another embodiment, the adapter 20 includes at least one securing member support 22. As shown, two securing member supports 22 are illustrated on opposite sides of the access 27. It will be appreciated that additional supports may be employed as desired or necessary for supporting the securing member on the adapter 20, and may be disposed in other locations on the adapter 20 than that illustrated. The securing member supports 22 engage the securing member 30 to hold the elongated body 12 and adapter 20 in a position such that an airway of the patient remains open. As one preferred example only, the securing member supports 22 are protrusions or prongs extending outward from the trailing end 16 in the same direction as the extended portion 28. The prongs 22 attach the securing member 30 through the securing holes 32 to connect the adapter 20 to the securing member 30.

It will be appreciated, however, that the prong and hole structure is merely exemplary as other securing methods may be employed that are equally or more suitable. It will be further appreciated that in any event where an adapter is not employed, the securing member 30 may also be attached to the elongated body 12 directly. Such as, for instance, in a configuration where there is no separate adapter piece, and where the elongated body 12 includes an extended portion and access integrally formed thereon, and the elongated body 12 includes securing member supports integrally formed thereon.

In another embodiment, the adapter 20 defines at least one aperture therethrough. As shown, the adapter 20 includes two apertures 24 oppositely disposed of the access 27. The apertures 24 enable support of first and second flow conduits 44, 54. Preferably, the flow conduits 44, 54 are capable of delivering a supplemented supply of oxygen, and are capable of monitoring end tidal carbon dioxide along side surfaces of the elongated body 12.

As one example, the first flow conduit 44 may be a tubing insertable through one of the apertures 24. Preferably, the flow conduit 44 is constructed of a reinforced material so that, in the event of bite down by the patient, the flow conduit 44 will not collapse or be obstructed. It will be appreciated that the flow conduit 44 is a reinforced material and may be similar to the plastic material of the elongated body 12. It will be further appreciated that the flow conduit 44 is to be suitably rigid for patient use and for preventing such undesired effects. The flow conduit 44 may be disposed along a side groove 12a of the elongated body 12. The side groove 12a supports the flow conduit along a side surface of the elongated body 12. An inserted end of the first conduit 44 may enable carbon dioxide to be released therein, so that $ETCO_2$ may be monitored. The opposite end may include a first fitment 44a that connects with a carbon dioxide detector (not shown) to monitor $ETCO_2$.

With such capability, the apparatus 10 may monitor a patient's oxygenation more effectively, so that oxygen can be delivered sooner to a patient in need. When the $ETCO_2$ increases for example, then the oxygen level decreases. In previous applications, oxygen levels had been monitored by pulse oximetry. Such methods, however, have required waiting on a perfusion time of 15-30 seconds. In the embodiment provided by the apparatus 10, oxygen levels can be determined at a sooner time, so that oxygen may be delivered to a patient before a critical point of need.

As another example, the second flow conduit 54 may be a tubing insertable through the other one of the apertures 24. Preferably, the flow conduit 54 is constructed of a reinforced material so that, in the event of bite down by the patient, the flow conduit 54 will not collapse or be obstructed. It will be appreciated that the flow conduit 54 is a reinforced material and may be similar to the plastic material of the elongated body. It will be further appreciated that the flow conduit 54 is to be suitably rigid for patient use and for preventing such undesired effects. The flow conduit 54 may be along another side groove 12a of the elongated body 12. The side groove 12a supports the flow conduit along a side surface of the elongated body 12. An inserted end of the second conduit 54 may exit a supplement supply of oxygen that is delivered to the patient. The opposite end may include a second fitment 54a that connects with an oxygen supply source (not shown). While flow conduit 44 has been described for $ETCO_2$ monitoring and flow conduit 54 has been described for oxygen delivery, it will be appreciated that either flow conduit 44, 54 may be used for any delivery or monitoring purpose, and that flow conduit 44 is not limited to $ETCO_2$ monitoring and that flow conduit 54 is not limited to oxygen delivery.

Although two flow conduits are shown, it will be appreciated that more or less than two conduits may be employed as necessary or desired for delivery of other fluids or for other monitoring purposes. It will be appreciated that supplying oxygen and monitoring end tidal carbon dioxide are some preferred examples only of fluids that the apparatus supports. It may be desirable to deliver or monitor other fluids including other gases and liquids. The term "fluid" is construed broadly to include any medium that can be made to flow.

The adapter 20 may be constructed from any number of materials, including but not limited to molded soft plastics. The adapter may be constructed of any material that is suitably rigid and similar to the elongated body 12 for maintaining an open airway of the patient. It will be appreciated that such materials are exemplary only, as other materials may be equally or more suitable. It will further be appreciated that the adapter 20 may be integrally formed with the elongated body 12, whereby the elongated body 12 and adapter 20 may be represented as a one piece unit.

In yet another embodiment, the elongated body 12 includes a lead portion 18 proximate the leading end 12. Preferably, the lead portion 18 defines an arching portion. The arching portion defines an overcurve and an undercurve. The overcurve is configured to contact the upper ridge of a patient's mouth at the hard palate and just before the soft palate. The undercurve is configured to contact the tongue of the patient. The arching portion enables the elongated body 12 to maintain a tongue of the patient in a posterior position. In one preferred example, the lead portion 18 is configured of a length such that its arching configuration does not extend deep enough into the soft palate, and so as to prevent a gag reflex by a patient when the elongated body 12 is inserted.

In another embodiment of the elongated body 12, a flange 16a is disposed at the trailing end 16. Preferably, the flange 16a is annularly disposed about the outer surface of the elongated body 12. The flange 16a may enable a patient to comfortably fit the apparatus 10 around his/her mouth, and help to prevent the entire apparatus 10 from entering the patient.

FIGS. 6-10 illustrate another embodiment of an apparatus 100 for maintaining a surgical airway. Similar to apparatus 10, the apparatus 100 includes an elongated body 112 defining a leading end 114 with a lead portion 118 that is arched and a trailing end 116 with a trailing portion 119. The elongated body 112 includes an opening 117 defined through the leading and trailing ends 114, 116. Further, the apparatus 100 includes securing member supports 122 that are configured to engage a securing member (not shown) to secure the apparatus 100 in a position to maintain an open airway of a patient. In one exemplary embodiment and similar to apparatus 10, the securing member supports 122 are protrusions or prongs disposed on a flange 126 (further described below), and extend outward from the trailing end 116. While a securing member is not shown, it will be appreciated that the securing member 30 for apparatus 10 may be suitably employed with the securing member supports 122 in a similar manner already described.

An extended portion 128 is disposed at the trailing end 116 of the elongated body 112, and extends outward and away from the elongated body 112. The extended portion 128 is configured to be positioned such that it can extend outward from the patient's mouth, when the apparatus 100 is inserted into a patient's mouth. The extended portion 128 includes an access 127 that is configured to allow surgical equipment and treatment materials to be inserted therethrough and into and through the opening 117 of the elongated body 112. As one example only, the extended portion 128 is a hollow cylindrical structure which defines the access 127. The access 127 extends toward the opening 117, where a passageway defined from the trailing end 116 to the leading end 114 widens, when the opening defined by the access 127 reaches the opening 117. In this configuration, the widened passageway can help prevent undercuts during molding and forming of the apparatus. It will be appreciated that the shape of the extended portion 128 and access 127 are not limited to a specific structure, so long as the extended portion 128 enables the access 127 to allow surgical equipment therethrough and into the opening 117 of the elongated body 112.

The flange 126 is disposed proximate the trailing end 116 and is positioned between the elongated body 112 and the extended portion 128. As shown, the flange 126 is an oval-like shape that is annularly disposed about the elongated body 112. The flange 126 may provide a face plate structure so as to enable a patient to comfortably fit the apparatus 100 around his/her mouth, while preventing the entire apparatus 100 from being inserted into the patient's mouth. As one example only, the flange 126 has an arched configuration that is convex facing the trailing end 116 and concave facing the leading end 114. This arched configuration can provide a more comfortable fit of the apparatus 100, where the flange 126 resides external to the patient's mouth and on his/her face. It will be appreciated that the flange 126 is not limited to the specific structure shown and may be suitably modified to achieve the comfortable fit desired, while preventing the entire apparatus from being inserted into a patient's mouth.

Figure 7:
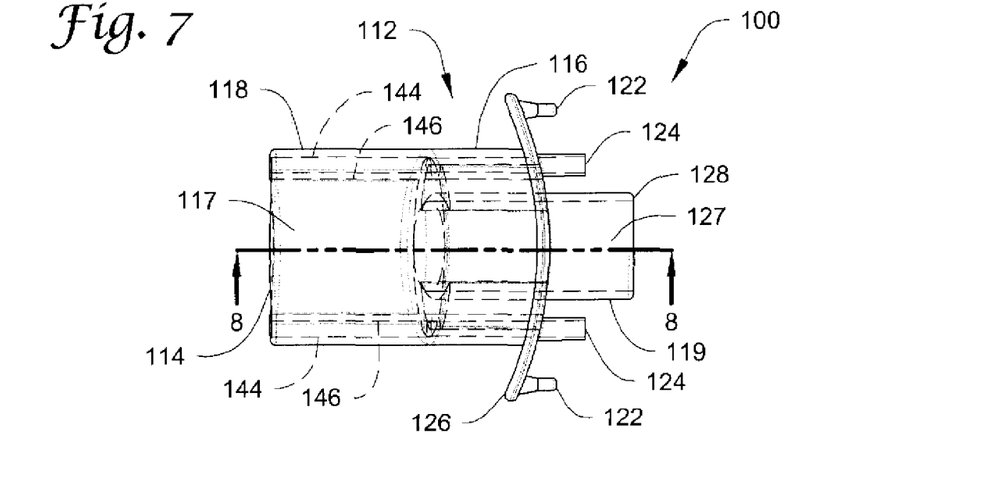
FIG. 7 represents an elevated top view of the apparatus of FIG. 6.
Figure 8:
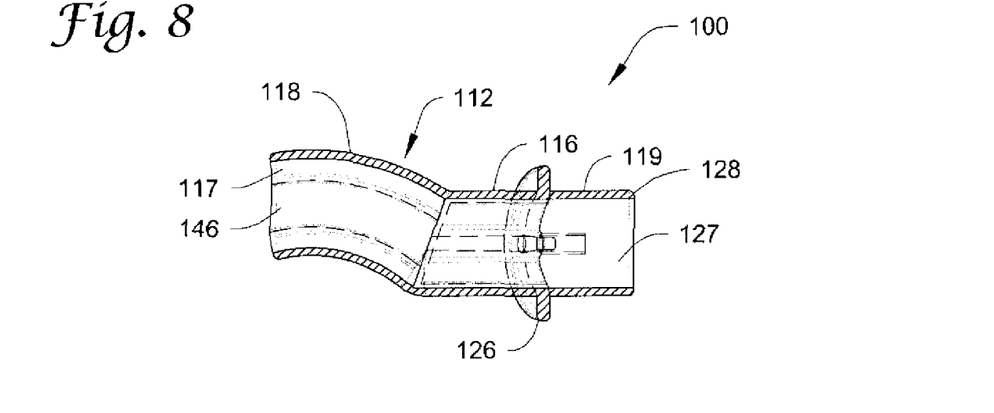
FIG. 8 represents an elevated side sectional view of the apparatus of FIG. 6 taken from line 8-8 of FIG. 7.
Figure 9:
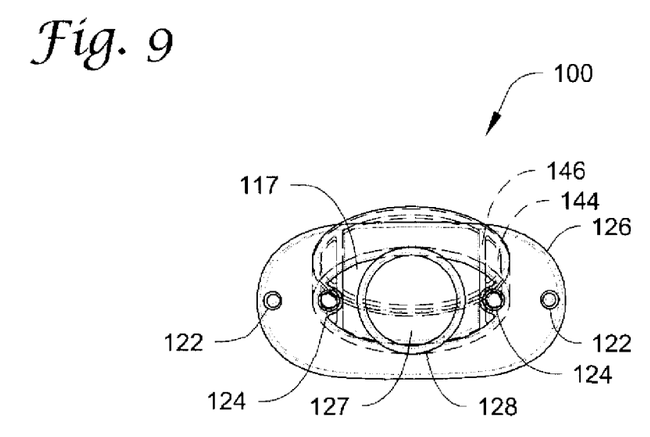
FIG. 9 represents an elevated front perspective view of the apparatus of FIG. 6 taken from line 9-9 of FIG. 6.
Figure 10:
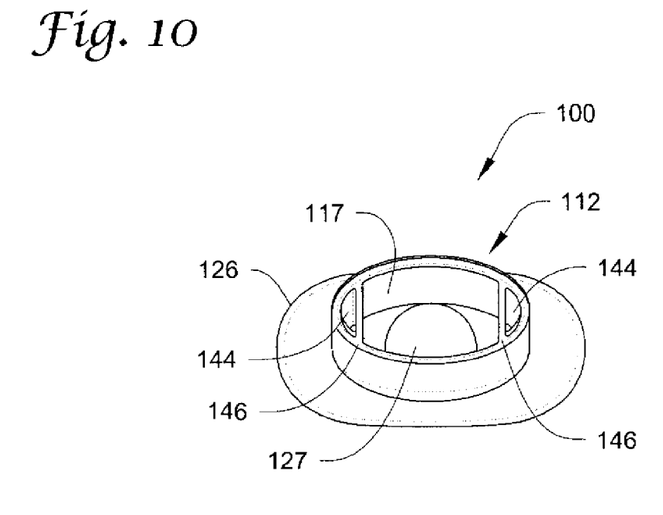
FIG. 10 represents an elevated rear perspective view of the apparatus of FIG. 6 taken from line 10-10 of FIG. 6.
Figure 11:
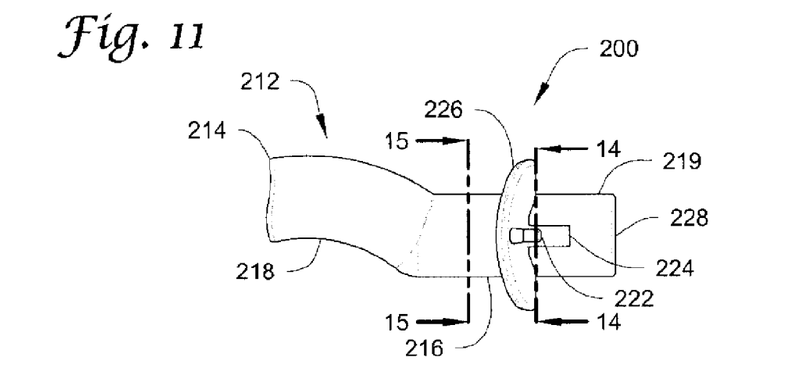
FIG. 11 represents an elevated side view of another embodiment of an apparatus for maintaining a surgical airway.

The flange 126 includes apertures 124 that extend through the flange 126 and into the elongated body 112. As best shown in FIGS. 7 and 9, the apertures 124 are defined by outward extending prongs having openings therethrough to the elongated body 112. The prong structure can allow for tubings or fitments (not shown) to be attached so as to access the apertures 124. It will be appreciated that such tubings and fitments are known and that any of the tubings and fitments previously described may be suitably attached to access the apertures 124. It will be appreciated that the prong structure shown is merely exemplary, and that the apertures are not limited to any specific structure, so long as they enable access to flow channels 144 (described in detail below).

As mentioned, the apertures 124 allow access to the flow channels 144 in the elongated body 112. FIG. 9 illustrates the apertures 124 extending through the flange 126 (shown in phantom line) to the flow channels 144 inside the elongated body 112. As best shown in FIGS. 7-10, the flow channels 144 are formed within the elongated body 112 as distinct channels separated from the opening 117 or main opening. Walls 146 formed within the elongated body 112 separate the flow channels 144 from the opening 117. In this configuration, the flow channels are formed as a part of the elongated body 112, where the opening 117 and the flow channels 144 provide distinct lumens through the elongated body 112. The flow channels 144 can allow for a more universal apparatus to maintain an airway that is not specific for any particular tubing, and may be adaptable with any desired tubing to attach to the prong structure where the apertures 124 are disposed. As one preferred example, the channels 144 are configured to allow delivery and monitoring of the patient, such as delivering oxygen to the patient and monitoring a patient's $ETCO_2$. In this manner, the flow channels 144 can operate similarly to the tubing flow conduits 44, 54 already described.

As shown, the flow channels 144 are disposed as two flow channels at opposite sides of the elongated body 112. The flow channels 144 are disposed adjacent the opening 117 and proximate sides of inner surfaces the elongated body 112. It will be appreciated that only one flow channel or more than two flow channels may be formed in the elongated body 112. It further will be appreciated that the flow channels 144 shown are not limited to being positioned at opposite sides or in any specific orientation, so long as they are formed within the elongated body 112.

FIGS. 11-15 illustrate another embodiment of an apparatus 200 for maintaining a surgical airway. The apparatus 200 is similar to the apparatus 100, except that the apparatus 200 includes smaller scaled passages than the apparatus 100. That is, the access 227, the opening 217, and the flow channels 244 may be constructed of a smaller scale than the apparatus 100. It will be appreciated that the scale of the passages and the overall size of the embodiments described may be modified as necessary to accommodate a patient's use. As with apparatus 100, apparatus 200 includes an elongated body 212 defining a leading end 214 with a lead portion 218 that is arched and a trailing end 216 with a trailing portion 219. The elongated body 212 includes an opening 217 defined through the leading and trailing ends 214, 216. Further, the apparatus 200 includes securing member supports 222 that are configured to engage a securing member (not shown) to secure the apparatus 200 in a position to maintain an open airway of a patient. As with apparatus 100, the securing member supports 222 are protrusions or prongs disposed on a flange 226 that extend outward from the trailing end 216, and it will be appreciated that the securing member 30 for apparatus 10 may be suitably employed with the securing member supports 222 as already described.

An extended portion 228 is disposed at the trailing end 216 of the elongated body 212, and extends outward and away from the elongated body 212. The extended portion 228 is configured to be positioned such that it can extend outward from the patient's mouth, when the apparatus 200 is inserted into a patient's mouth. The extended portion 228 includes an access 227 that is configured to allow surgical equipment and treatment materials to be inserted therethrough and into and through the opening 217 of the elongated body 212.

The flange 226 is disposed proximate the trailing end 216 and is positioned between the elongated body 212 and the extended portion 228. The flange 226 may provide a face plate structure so as to enable a patient to comfortably fit the apparatus 200 around his/her mouth, while preventing the entire apparatus 200 from being inserted into the patient's mouth. As one example only, the flange 226 also includes an arched configuration that is convex facing the trailing end 216 and concave facing the leading end 214.

Figure 12:
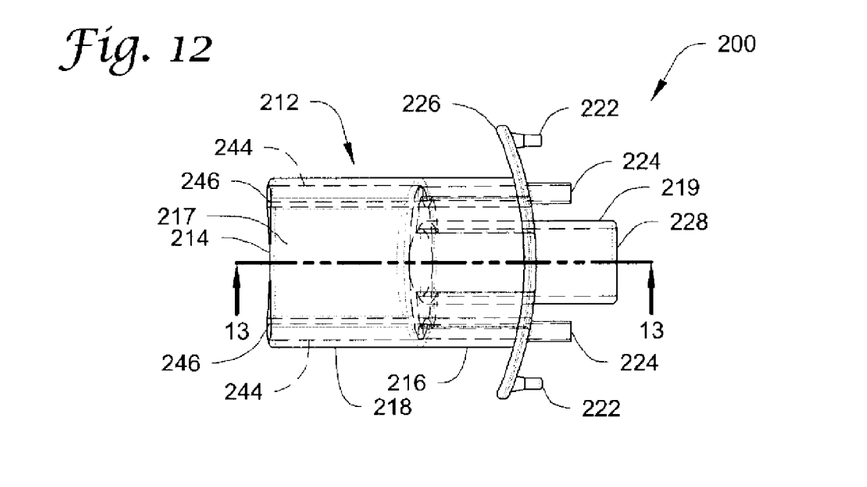
FIG. 12 represents an elevated top view of the apparatus of FIG. 11.
Figure 13:
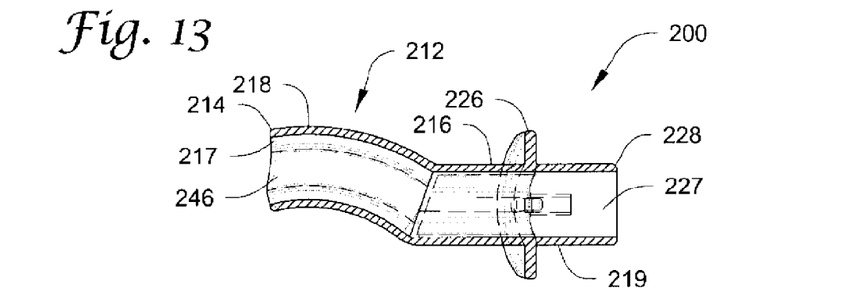
FIG. 13 represents an elevated side sectional view of the apparatus of FIG. 11 taken from line 13-13 of FIG. 12.
Figure 14:
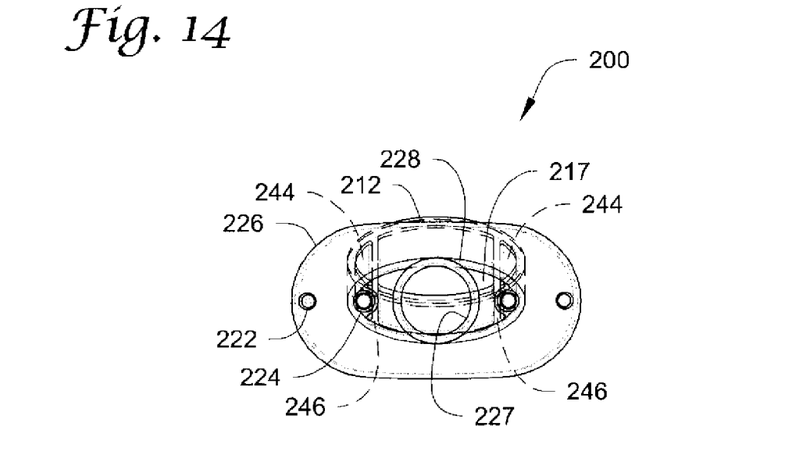
FIG. 14 represents an elevated front perspective view of the apparatus of FIG. 11 taken from line 14-14 of FIG. 11.
Figure 15:
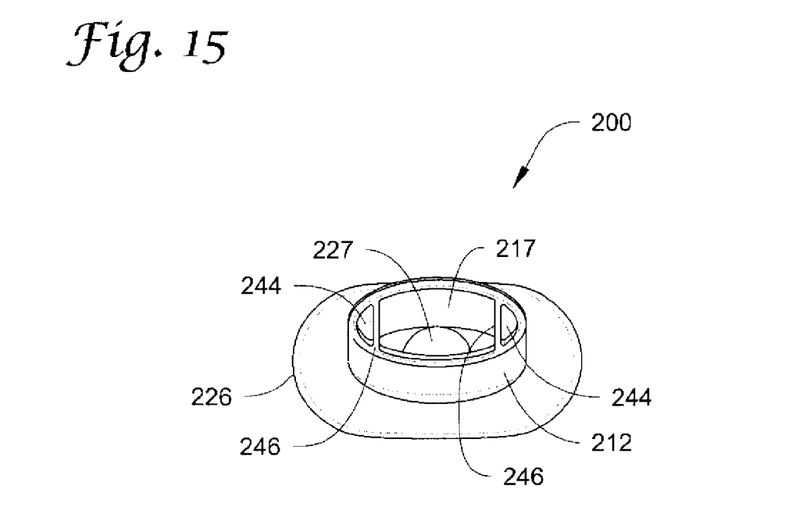
FIG. 15 represents an elevated rear perspective view of the apparatus of FIG. 11 taken from line 15-15 of FIG. 11.
Figure 16:
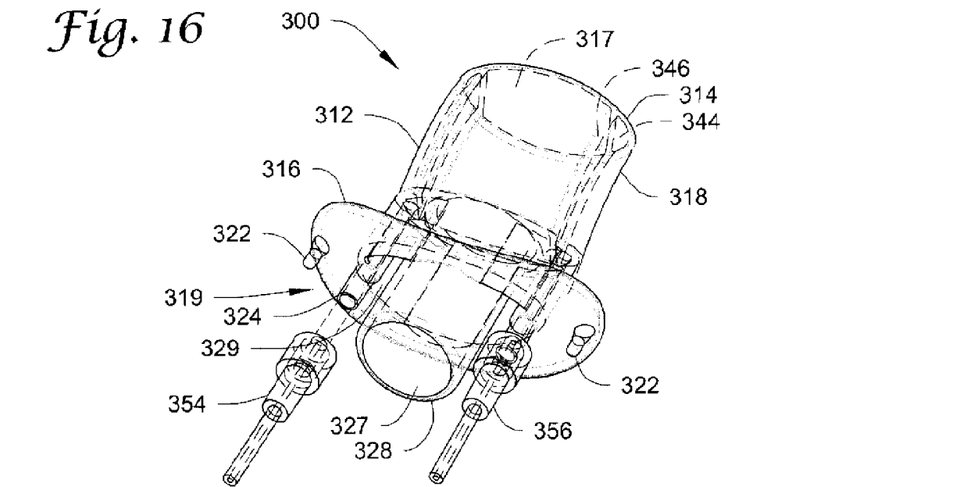
FIG. 16 represents an elevated front perspective view of another embodiment of an apparatus for maintaining a surgical airway.
Figure 17:
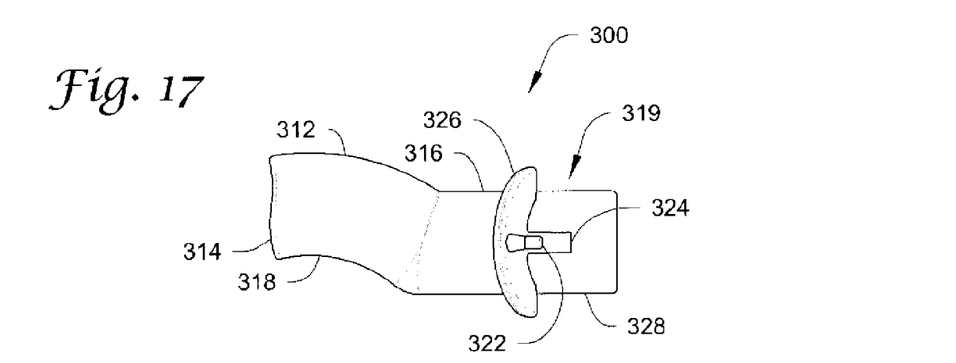
FIG. 17 represents an elevated side view of the apparatus of FIG. 16.

The flange 226 includes apertures 224 that extend through the flange 226 and into the elongated body 212. As best shown in FIGS. 12 and 14, the apertures 224 also are defined by outward extending prongs having openings therethrough to the elongated body 212. The prong structure can allow for tubings or fitments (not shown) to be attached so as to access the apertures 224.

The apertures 224 allow access to flow channels 244 in the elongated body 212. FIG. 14 illustrates the apertures 224 extending through the flange 226 (shown in phantom line) to the flow channels 244 inside the elongated body 212. As best shown in FIGS. 12-15, the flow channels 244 are formed within the elongated body 212 as distinct channels separated from the opening 217 or main opening. Walls 246 formed within the elongated body 212 that separate the flow channels 244 from the opening 217. In this configuration as well, the flow channels 244 are formed as a part of the elongated body 212, where the opening 217 and the flow channels 244 provide distinct lumens through the elongated body 212.

FIGS. 16-20 illustrate another embodiment of an apparatus 300 for maintaining a surgical airway. The apparatus 300 is similar to the apparatuses 100 and 200, while further including a cored out area 329 and showing how fitment structures may be connected to the apparatus. The cored out area 329 is disposed about an extended portion 328 and proximate a trailing end 316. The cored out area 329 extends through a flange 326 and terminates at an opening 317 in the elongated body 312 (best shown in FIGS. 18-19). In this configuration, the cored out area 329 can help facilitate the apparatus being formed as a single integrally molded part.

Further, fitments 354, 356 are also shown attached to the prong structure of aperture 324. In one example only, fitment 354 is connected with the aperture via a tubing 358 that is inserted into the flange 326 to access flow channels 344. In another example, fitment 356 is fixed to the flange 326 at the aperture 324. It will be appreciated that a fitment that is to be fixed to the flange (i.e. fitment 356) may be attached in any number of ways, such as but not limited to a press fit or glue configuration. As with fitment 354, fitment 356 may include tubing that is insertable into the aperture to access the flow channels 344.

As with apparatuses 100 and 200, apparatus 300 includes an elongated body 312 defining a leading end 314 with a lead portion 318 that is arched and the trailing end 316 with a trailing portion 319. The elongated body 312 includes an opening 317 defined through the leading and trailing ends 314, 316. Further, the apparatus 300 includes securing member supports 322 that are configured to engage a securing member as already described.

The extended portion 328 is disposed at the trailing end 316 of the elongated body 312, and extends outward and away from the elongated body 312. The extended portion 328 is configured to be positioned such that it can extend outward from the patient's mouth, when the apparatus 300 is inserted into a patient's mouth. The extended portion 328 includes an access 327 that is configured to allow surgical equipment and treatment materials to be inserted therethrough and into the opening 317 of the elongated body 312.

The flange 326 is disposed proximate the trailing end 316 and is positioned between the elongated body 312 and the extended portion 328. The flange 326 may provide a face plate structure so as to enable a patient to comfortably fit the apparatus 300 around his/her mouth, while preventing the entire apparatus 300 from being inserted into the patient's mouth. The flange 326 also includes an arched configuration that is convex facing the trailing end 316 and concave facing the leading end 314.

Figure 18:
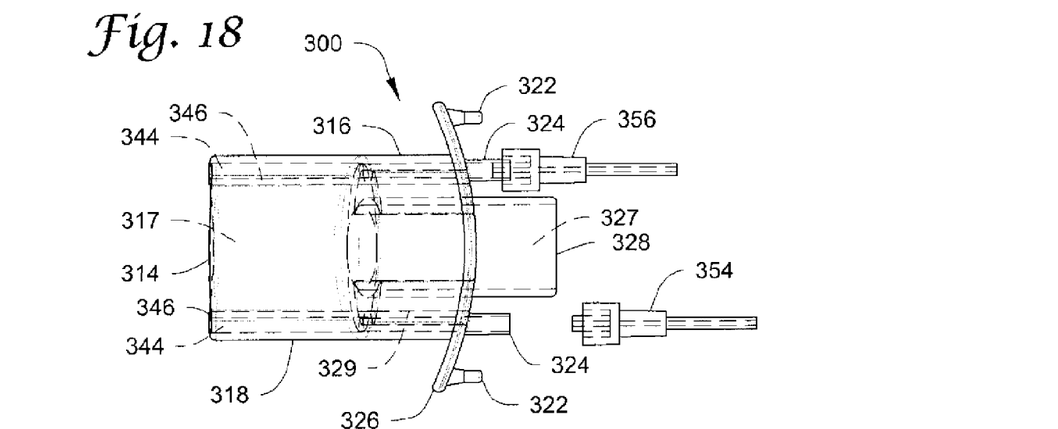
FIG. 18 represents an elevated top sectional view of the apparatus of FIG. 16.
Figure 19:
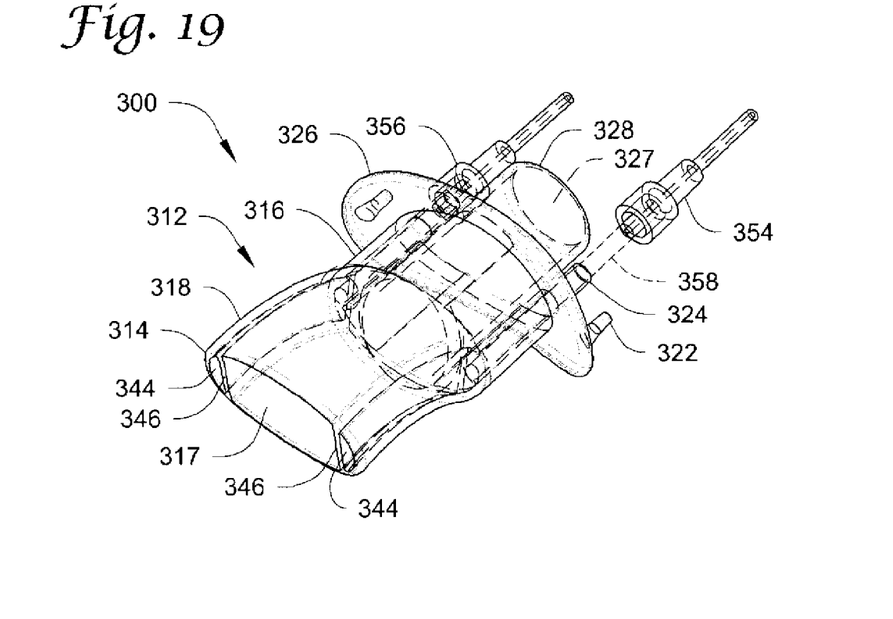
FIG. 19 represents an elevated rear perspective view of the apparatus of FIG. 16.
Figure 20:
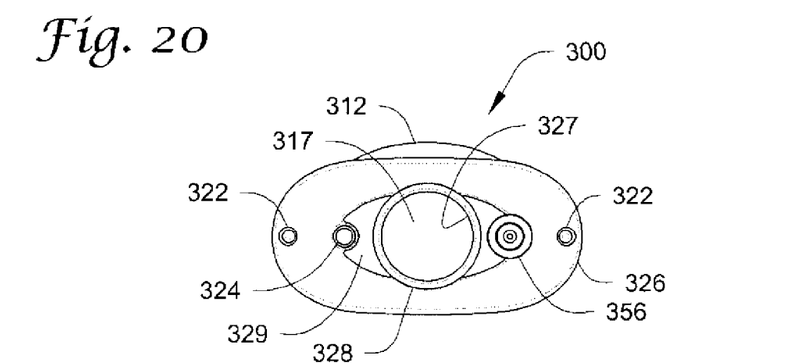
FIG. 20 represents an elevated front perspective view of the apparatus of FIG. 16.

The flange 326 includes the apertures 324 that extend through the flange 326 and into the elongated body 312. As one example which is best shown in FIGS. 18 and 19, the apertures 324 also are defined by outward extending prongs having openings therethrough to the elongated body 312. The prong structure allows for tubings or fitments (i.e. fitments 354, 356 and tubings 358) to be attached so as to access the apertures 324.

As described, the apertures 324 allow access to flow channels 344 in the elongated body 312. FIG. 19 illustrates the apertures 324 extending through the flange 326 to the flow channels 344 inside the elongated body 312. The flow channels 344 are formed within the elongated body 312 as distinct channels separated from the opening 317 or main opening. Walls 346 also are formed within the elongated body 312 that separate the flow channels 344 from the opening 317. In this configuration as well, the flow channels 344 are formed as a part of the elongated body 312, where the opening 317 and the flow channels 344 provide distinct lumens through the elongated body 312.

As one preferred example only, the apparatuses 100, 200, and 300 may be constructed of an injection molded material that is medically approved, such as but not limited to a medically approved plastic material. The material may be, but is not limited to, an approved polypropylene material. It will be appreciated that the apparatuses 100, 200, and 300 also may employ any of the materials suitable for apparatus 10 as already described. In the configurations shown, the apparatuses 100, 200, and 300 may be formed such that the elongated body (including the opening and flow channels), the flange, and the extended portion are all constructed as a one-piece unitary structure that is injection molded. Differently from apparatus 10 shown in FIGS. 1-5, the apparatuses 100, 200, and 300 do not include a separate adapter component, as the flange and extended portion are integrally formed as a one-piece structure with the elongated body. Further, the flow channels are formed within the elongated body and are not disposed as separate flow conduits along outer side surfaces of the elongated body.

The embodiments described above can provide an improved apparatus for maintaining an open airway with many benefits. For example, the elongated body with its rigid outer structure provides a bite block to prevent a patient from closing his/her mouth and prevents the airway from collapsing. Thus, the bite block function facilitates maintaining the airway in an open position. In conditions where a patient may experience a seizure, for example, the outer structure of the elongated body prevents the opening from collapsing even when a patient bites down on the apparatus. As one preferred example, any of the apparatuses described may be constructed and arranged for one-time use, such as for use on a per patient basis.

Any of the described apparatuses may include a variety of dimensions suitable for both adults and children. As an example for adult sizes, the elongated body may include a length from leading end to trailing end that is approximately 4.0 inches, and in one preferred example approximately 3.5 inches. A length of the insertable portion of the elongated body may be approximately 2.5 inches. A width of the elongated body may have a range from approximately 1.0 inches to approximately 2.0 inches and suitable for both males and females. The width of the elongated body including the flange may be approximately 2.5 inches to approximately 3.0 inches. A height or thickness of the elongated body alone may be approximately 0.75 inches to approximately 1.0 inches. A height of the elongated body including the flange may be approximately 1.5 inches. The opening within the elongated body may include a width of approximately 1⅛ inches. In some other examples, the opening may include a width of approximately 1.3 inches. If a separate adapter is used (FIGS.

Figure 1:
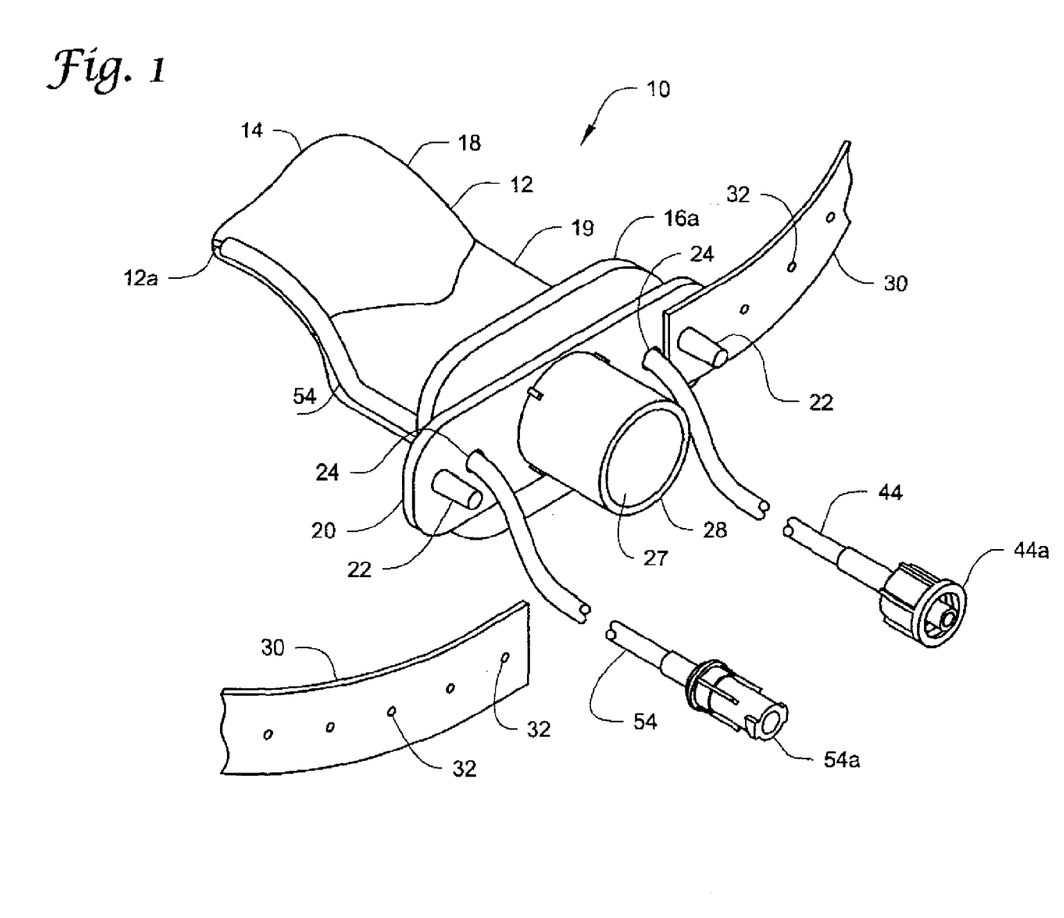
FIG. 1 represents an elevated perspective view of one embodiment of an apparatus for maintaining a surgical airway.
Figure 2:
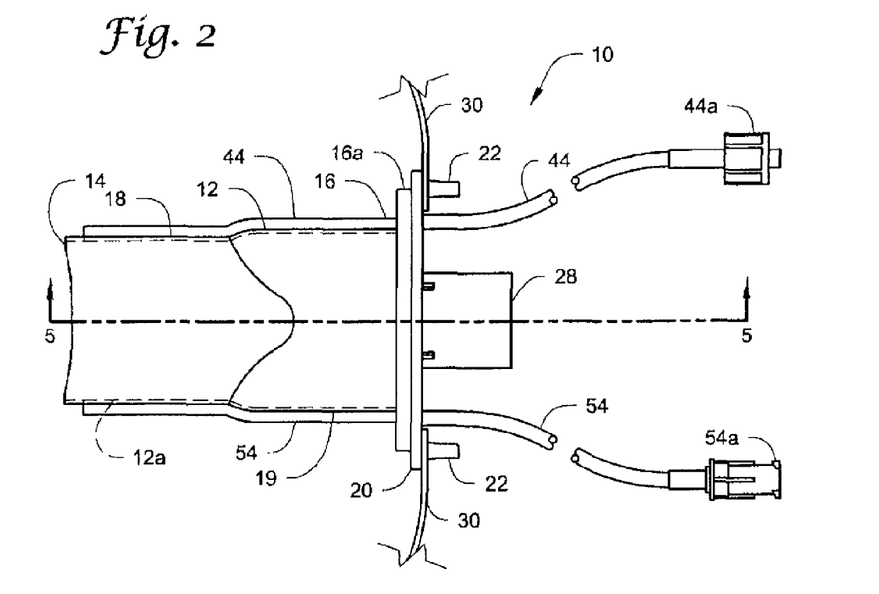
FIG. 2 represents an elevated top view of the apparatus of FIG. 1.
Figure 3:
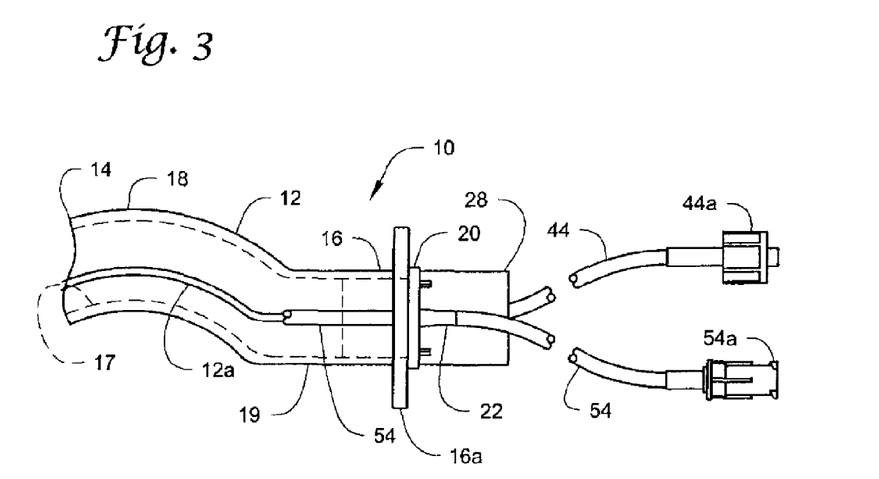
FIG. 3 represents an elevated side view of the apparatus of FIG. 1.
Figure 4:
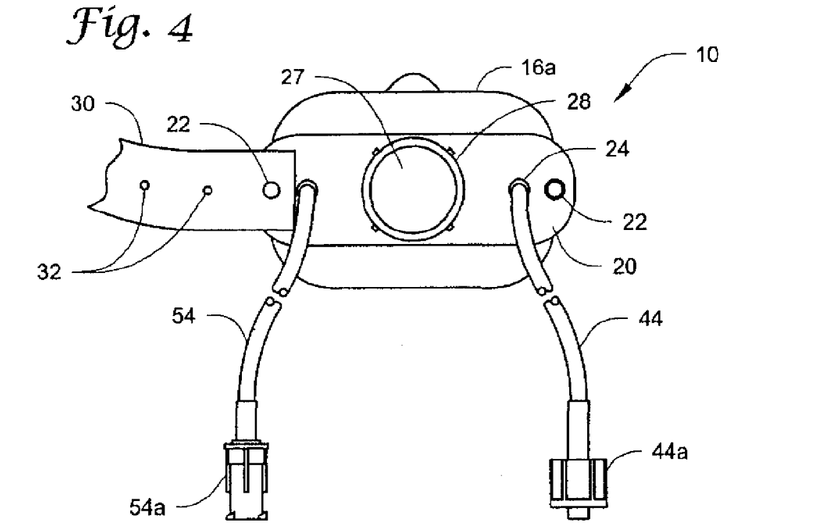
FIG. 4 represents an end view of the apparatus of FIG. 1 showing one embodiment of a leading end.
Figure 5:
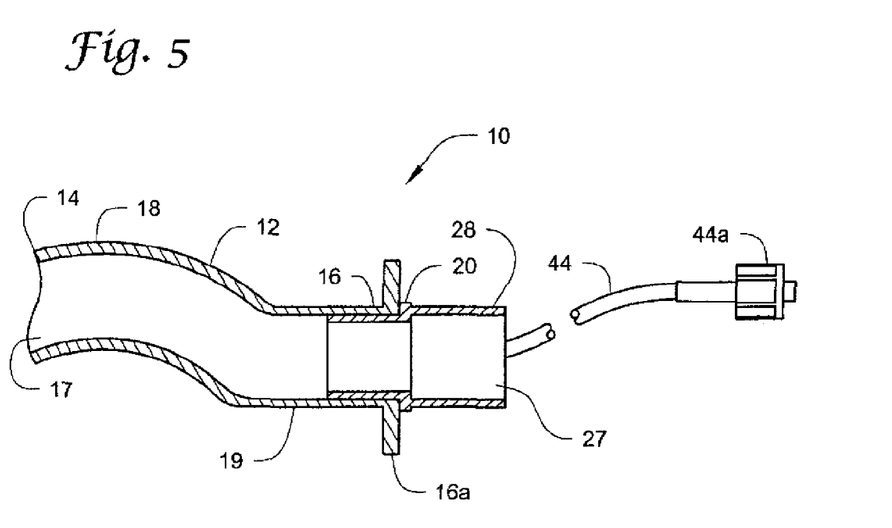
FIG. 5 represents a side sectional view of the apparatus of FIG. 1.
Figure 6:
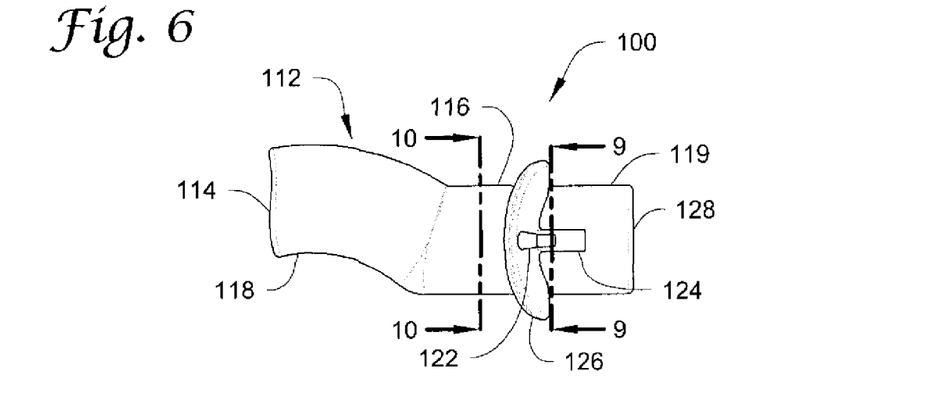
FIG. 6 represents an elevated side view of another embodiment of an apparatus for maintaining a surgical airway.

1-5), a height of an access of the adapter may approximately have a range of approximately ⅝ inches to approximately ½ inches. As some other examples without a separate adapter piece (FIGS. 6-21), the access to the opening of the elongated body may have a width of approximately ⅝ inches to approximately 1.0 inches.

It will be appreciated, however, that such dimensions are exemplary only. Other dimensions may be employed that are equally or more suitable to achieve the desired functions of the above embodiments. Thus, the dimensions of any of the described apparatuses, and particularly of the elongated body, are only limited to provide appropriate sizes related to a patient's age and gender, and may be suitably sized as necessary to fit a patient for optimal results.

The embodiments described provide a more secure surgical airway that may be disposed after one-time use. The elongated body provides a structure that includes bite block protection and keeps the tongue from obstructing the airway (oral pharynx). The apparatus is capable for monitoring $ETCO_2$ of a patient. Supplemental oxygen flow may be provided to the patient at a higher concentration and at improved rates, without impeding access to the airway. The apparatus provides that oxygen concentrations may be improved as high as 60-80%. Furthermore, the apparatus for maintaining a surgical airway requires less equipment for its use, for example, no mask is required to cover a patient's face. The apparatus provides an elegant design with improved performance and user convenience.

The apparatus may be employed in known medical procedures, such as but not limited to, gastro and/or bronchial surgical procedures, and may be employed in outpatient applications, for instance, where patients experience sleep apnea. As some additional examples only, such procedures and applications may include use in esophago-gastro dilatations (EGDs), gastroscopies, bronchoscopies, and in deep monitored anesthesia care (MAC) cases. It will be appreciated that the apparatus may be employed in any number of applications and procedures, and is not limited to those listed. It will be appreciated that any procedure requiring an open airway of a patient to be maintained may employ the apparatus as already described.

The above specification provides a complete description of the composition, manufacture and use of an improved apparatus for maintaining a surgical airway in accordance with the principles of the present invention. Since many embodiments an apparatus for maintaining a surgical airway can be made without departing from the spirit and scope of the invention, the invention resides in the claims hereinafter appended.

The invention claimed is:

1. An apparatus for maintaining a surgical airway orally through a patient, comprising:

an elongated body insertable orally into a patient, the elongated body including, a first end and a second end, one of the first or second ends defining a leading end insertable orally into a patient, the other of the first and second ends defining a trailing end including a main opening disposed through the elongated body and between the leading and trailing end, the main opening enabling insertion of surgical equipment therethrough for use in treatment of the patient, and the opening supporting airflow to the patient, two flow conduits disposed adjacent the main opening along and proximate to the sides of an inner surface of the elongated body;

a flange integrally formed with the elongated body at the trailing end, wherein the flange comprises a main access to the main opening, two accesses to the two flow conduits, the two accesses forming prongs which extend outward relative to the trailing end and the flange, and two securing member supports, the member supports being protrusions that extend outward relative to the trailing end and flange, wherein the flange, elongated body, main opening, flow conduits and securing member supports are constructed as a one-piece unitary structure;

a securing member connected to the trailing end by the securing member supports, the securing member supports are adapted to engage the securing member so as to hold the elongated body in position so that an airway of the patient remains open when the elongated body is orally inserted into the patient, the securing member comprises a resilient strap adapted to be dressed around the head or lower neck of the patient, the resilient strap includes a plurality of holes, so that the resilient strap is adapted to be removably attached to the securing member supports;

one of the flow conduits is deliverable of oxygen to the patient, so as to maintain oxygen to the patient during operating or surgical procedures, the other flow conduit is receivable of carbon dioxide from the patient, so as to enable monitoring of end tidal carbon dioxide of the patient, wherein one of the two flow conduits is disposed between the main access and one of the securing member supports, and the other of the two flow conduits is disposed between the main access and the other of the securing member supports.

2. The apparatus according to claim 1 wherein the resilient strap includes a plurality of securing holes, so that the resilient strap is removably attached with the elongate body.

3. The apparatus according to claim 1 wherein the flange is configured so as not to enter a mouth of the patient when the elongated body is inserted into the patient.

4. The apparatus of claim 1 wherein the securing member supports are arranged beyond the width of the elongated body when the apparatus is viewed from a top view.

* * * * *